United States Patent [19]
El-Rashidy et al.

[11] Patent Number: 5,830,500
[45] Date of Patent: Nov. 3, 1998

[54] LOW DOSE FLUOXETINE TABLET

[75] Inventors: Ragab El-Rashidy, Deerfield; Bruce Ronsen, River Forest, both of Ill.

[73] Assignee: Pentech Pharmaceuticals, Inc., Wheeling, Ill.

[21] Appl. No.: 681,276

[22] Filed: Jul. 22, 1996

[51] Int. Cl.⁶ .................................................. A61K 9/20
[52] U.S. Cl. ............................................................ 424/465
[58] Field of Search .................................. 424/462, 474, 424/465

[56] References Cited

U.S. PATENT DOCUMENTS

| | | | |
|---|---|---|---|
| 4,018,895 | 4/1977 | Molloy et al. | 514/649 |
| 4,035,511 | 7/1977 | Messing et al. | 514/651 |
| 4,083,982 | 4/1978 | Messing et al. | 514/282 |
| 4,194,009 | 3/1980 | Molloy et al. | 514/651 |
| 4,314,081 | 2/1982 | Molloy et al. | 564/347 |
| 4,329,356 | 5/1982 | Holland | 514/419 |
| 4,590,213 | 5/1986 | Stark | 514/653 |
| 4,594,358 | 6/1986 | Hynes | 514/651 |
| 4,609,758 | 9/1986 | Husbands | 564/348 |
| 4,626,549 | 12/1986 | Molloy et al. | 514/651 |
| 4,647,591 | 3/1987 | Cherkin et al. | 514/651 |
| 4,683,235 | 7/1987 | Hynes | 514/282 |
| 4,956,361 | 9/1990 | Traber et al. | 514/217 |
| 5,151,448 | 9/1992 | Crenshaw et al. | 514/651 |

OTHER PUBLICATIONS

Wong, D.T. et al., Life Sciences 57(5):411–441 (1995).

*Primary Examiner*—Peter F. Kulkosky
*Attorney, Agent, or Firm*—Olson & Hierl, Ltd.

[57] ABSTRACT

A direct compression tablet exhibiting relatively low hardness provides a relatively rapid release of fluoxetine. The tablet has a hardness of no more than about 6 kilopascals and a dicalcium phosphate dihydrate-to-disintegrant weight ratio of about 3 to about 7.

8 Claims, 1 Drawing Sheet

LOW DOSE FLUOXETINE TABLET

FILED OF THE INVENTION

This invention relates to a low hardness, direct compression tablet that provides a relatively rapid release of a drug such as fluoxetine. This invention also provides a convenient treatment of premature ejaculation with a relatively low dose of fluoxetine.

BACKGROUND OF THE INVENTION

Premature ejaculation is a sexual dysfunction that has been variously estimated to effect up to 75 percent of the population (Kinsey et al., 1949, p. 580; Masters and Johnson 1967, 1971 and 1973). Regardless of the figures in the literature and the definition of premature ejaculation, this problem has remained substantially unchanged in the past twenty years in the psychological, biochemical, pharmacological and clinical psychiatric literature. The term "premature ejaculation" includes congenital premature ejaculation as well as primary premature ejaculation where the male ejaculates extremely rapidly, e.g., prior to penetration with coitus or within ten to twenty strokes after intromission, so as to adversely affect the sexual relationship between the involved partners. The psychoanalytical definition of ejaculation, in less than one minute, also suffices for these purposes as well as the Masters and Johnson definition where the male ejaculates 50 percent (or more) of the time more rapidly than the female is able to have an orgasm if she has no orgasmic dysfunction of her own. Premature ejaculation by any of the foregoing definitions can be treated by the method of the invention.

Premature ejaculation is a considerable factor in sexual as well as marital discord. It is estimated that this factor is present in at least about 20 percent of clinical cases. Premature ejaculation can prevent or undermine stable relationships and marriage, and can promote depression, anxiety, and personality disorders. Premature ejaculation may also be associated with more severe sexual dysfunction, such as impotence, sexual aversion, lack of sexual desire, lack of orgasm in the partner and various paraphilia.

The current method of choice for treatment of premature ejaculation is behavior modification. The most commonly used technique provides limited long term benefit, with 25% of patients showing no improvement at the end of treatment, and 75% of patients showing no improvement at three years.

No drugs are currently approved by the FDA for the medical treatment of premature ejaculation. The use of anti-depressives for managing premature ejaculation has been explored informally by a few practitioners. Some limited success has been reported with the tricyclic antidepressant clomipramine (Anafranil). However, this medication has several problematic side effects such as weight gain, sedation, and anticholinergic effects, that have prevented wide use.

The use of fluoxetine for the treatment of premature ejaculation has been described by U.S. Pat. No. 5,151,448 to Crenshaw, which is incorporated herein by reference to the extent pertinent. A low dose, relatively quickly dissolving tablet that provides dissolution of about 50 weight percent of the active ingredient dose in about 1 minute is desired for practicing the aforementioned treatment.

SUMMARY OF THE INVENTION

A low hardness, direct compression tablet that is rapidly dissolving readily provides a relatively low dose of fluoxetine to a male patient and is useful for treating premature ejaculation. In a preferred embodiment, the present invention is a tablet that contains fluoxetine hydrochloride, calcium diphosphate dihydrate, a disintegrant and a lubricant. Dicalcium phosphate dihydrate and the disintegrant are present in a respective weight ratio in the range of about 3 to about 7.

Fluoxetine is preferably present as the hydrochloride salt, i.e., as fluoxetine hydrochloride. A preferred dosage is in the form of tablets providing the equivalent of about 7.5 mg to about 15 mg of fluoxetine base per tablet.

Premature ejaculation can be treated by a regimen of oral administration of such a low hardness, direct compression tablet formulation comprising a low dose of fluoxetine that provides dissolution rates that release about 50 weight percent of the fluoxetine present in about 1 minute. Rapid dissolution acts to facilitate bioavailability of the drug.

DETAILED DESCRIPTION OF PREFERRED EMBODIMENTS

Figure 1:
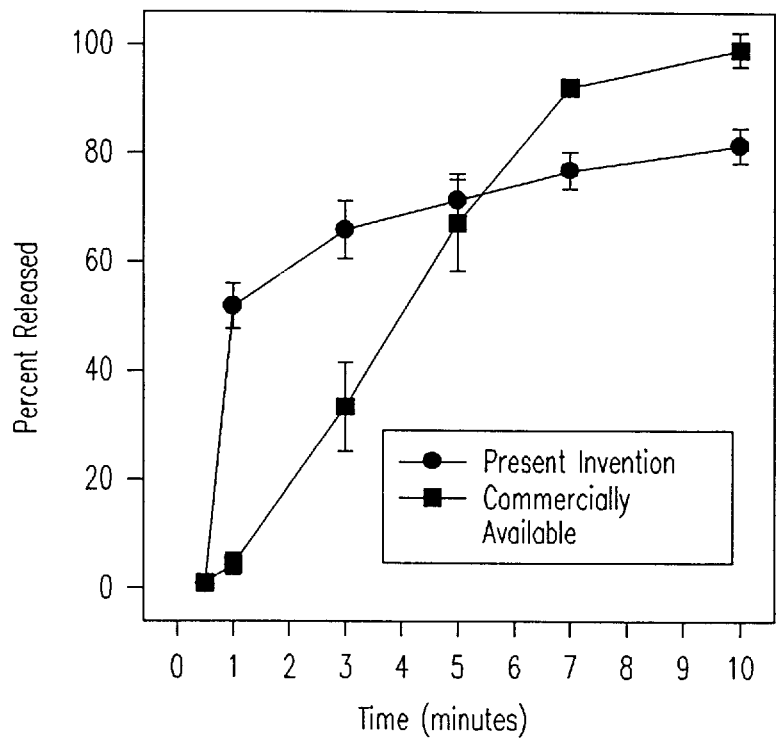
FIG. 1 is a graph of the dissolution of the dry compression fluoxetine composition of the present invention (filled circles), compared to that of a commercially available tablet (filled squares); error bars are ±1 standard deviation.

Fluoxetine is commercially available under the trade designation Prozac® as fluoxetine hydrochloride. This compound can be represented by the formula

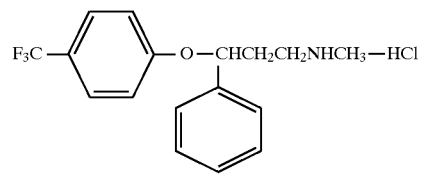

and is also known by its chemical name as (±)-N-methyl-3-phenyl-3-[(α,α,α-trifluoro-p-tolyl)-oxy]propylamine hydrochloride. The molecular weight of fluoxetine hydrochloride is 345.79. It is a white to off-white crystalline solid and exhibits a solubility in water of about 14 milligrams per milliliter.

The synthesis of fluoxetine and of the acid addition salts thereof is described, inter alia, in U.S. Pat. No. 4,194,009 to Molloy et al. Fluoxetine is an amine, and, as is well known, amines readily form acid addition salts with inorganic acids as well as organic acids.

The term "fluoxetine," as used herein and in the appended claims, means the free base form as well as an acid addition salt form of (±)-N-methyl-3-phenyl-3-[(α,α,α-trifluoro-p-tolyl)-oxy]propylamine. Such acid addition salts include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono- and dicarboxylates, phenyl-substituted alkanoates, hydroxy alkanoates and alkanedioates, aromatic acids, aliphatic and aromatic sulfonic acids, etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, 8-hydroxybutyrate, glycolate, malate, tartrate, methanesulfonate, propanesulfonates, naphthalene-1-sulfonate, naphthalene-2-sulfonate, mandelate and the like salts. Anti-anxiety drugs such as chlordiazepoxide (Librium®) and diazepam (Valium®) are not suitable for the treatment of premature ejaculation.

The specific dosage and duration of treatment may vary depending upon the particular patient. However, usually premature ejaculation is successfully treated by administering fluoxetine in a daily dose in the range of about 5 milligrams to about 80 milligrams for a time period of at least about 3 months, preferably for a time period of at least about 6 months. In some instances fluoxetine is administered chronically as long as the patient remains sexually active. A daily dose of about 20 milligrams is preferred.

The administered dosage can also vary over a period of time. A particularly preferred such treatment regimen contemplates the administration of a daily dose of about 30 milligrams for the first two weeks of treatment, then a daily dose of about 15–20 milligrams for the next four weeks of treatment, next a daily dose of about 10 milligrams for two weeks, followed by as per need (PRN) or precoital dose of about 10 milligrams for an extended time period as required.

The preferred formulation is a rapidly dissolving tablet of low hardness formed by direct compression. Suitable tablet hardness is no more than about 6 kilopascals (Kp) and usually is in the range of about 2.5 Kp to about 5.5 Kp. Preferably, tablet hardness is in the range of about 3.5 Kp to about 4.5 Kp. Most preferably, tablet hardness is about 4 Kp.

One preferred embodiment comprises fluoxetine HCl, a disintegrant, dicalcium phosphate dihydrate, and a lubricant. A preferred disintegrant is microcrystalline cellulose. Other suitable disintegrants for the present purposes are alginic acid, croscarmellose sodium, crospovidone, polacrilin potassium, sodium starch glycolate, starch, pregelatinized starches, sodium carboxymethyl celluloses, polyvinyl pyrrolidone, hydroxypropylmethyl cellulose, and sodium salt of polyacrylic acid. A preferred lubricant is magnesium stearate. The weight ratio of dicalcium phosphate dihydrate-to-disintegrant is in the range of about 3 to about 7. The preferred composition has a dicalcium phosphate dihydrate to microcrystalline cellulose weight ratio of about 5.

The preferred amount of fluoxetine present per tablet is in the range of about 7.5 milligrams to about 15 milligrams, expressed as fluoxetine base. A particularly preferred amount of fluoxetine per tablet is in the range of about 7.5 to about 10 milligrams, expressed as fluoxetine base.

The present tablets provide a rapid dissolution of fluoxetine, i.e., at least about 50 weight percent of the fluoxetine present in the tablet is released in about 1 minute.

The following examples are intended to illustrate, but not limit, the present invention.

EXAMPLE 1
Direct Compression Composition A

Composition A was formulated to provide the equivalent of 7.5 mg fluoxetine base per tablet. Compositions were mixed from dry ingredients and formed into tablets by the direct compression method. Composition A was prepared by weighing the amounts of the ingredients listed in Table 1, below. Each ingredient was passed through an appropriate sized screen: 30 mesh (dicalcium phosphate, microcrystalline cellulose) or 60 mesh (fluoxetine HCl, magnesium stearate). The fluoxetine HCl, dicalcium phosphate, and microcrystalline cellulose were placed into a blender and blended for 10 minutes. The magnesium stearate was added to the blender and mixed for an additional 2 minutes to yield a final powder mix. The final powder mix was transferred to a tableting machine equipped with the appropriate sized tooling and compressed into tablets.

EXAMPLE 2
Direct Compression Composition B

Composition B was formulated to provide the equivalent of 15 mg fluoxetine base. Composition B was prepared by weighing the amounts of the ingredients listed in Table 1, below, mixing the ingredients and forming tablets by the direct compression method as described in Example 1.

TABLE 1

Direct Compression Tablets

| Ingredient (mg/tablet) | Composition A 7.5 mg Fluoxetine Base | Composition B 15 mg Fluoxetine Base |
|---|---|---|
| Fluoxetine HCl | 8.38 | 16.77 |
| Dicalcium phosphate dihydrate, USP | 75.62 | 77.23 |
| Microcrystalline Cellulose, NF (Avicel PH102) | 15.0 | 15.0 |
| Magnesium Stearate, NF | 1.0 | 1.0 |
| TOTAL, mg/tablet | 100.00 | 110.00 |

EXAMPLE 3
Dissolution Testing

Dissolution of 6 tablets of Composition B, made by the method described in Example 1, was evaluated.

Dissolution was measured using USP Type II apparatus (USP XXIII) stirred at 30 rpm. The dissolution medium was 700 ml of distilled water at 37 degrees Celsius. Fluoxetine released into the medium was detected by absorbance at 225 nm. The tablets prepared were compared to a commercial soluble fluoxetine HCl tablet (Seronil 10 mg, Lot # 585398, Orion) for dissolution characterization. The results for 6 tablets of each formulation are presented as average percent release and standard deviation in Table 2, below.

TABLE 2

Dissolution Test 1

| | Present invention | | Commercially Available Tablet | |
|---|---|---|---|---|
| Time (min) | Average % Released | SD | Average % Released | SD |
| 0.5 | 3.1 | 0.5 | 4.0 | 0.4 |
| 10 | 61.3 | 7.2 | 83.6 | 5.1 |
| 15 | 85.5 | 6.3 | 94.6 | 3.6 |
| 20 | 90.2 | 5.1 | 96.6 | 3.4 |
| 30 | 93.4 | 4.4 | 97.8 | 3.4 |

Dissolution testing was repeated using the same measurement protocol at different time periods. The results for 6 tablets of each formulation are shown in Table 3 below and are graphically presented in FIG. 1.

TABLE 3

Dissolution Test 2

| Time (min) | Present invention Average % Released | SD | Commercially Available Tablet Average % Released | SD |
|---|---|---|---|---|
| 0.5 | 0.8 | 0.7 | 1.0 | 0.4 |
| 1 | 51.8 | 4.1 | 4.5 | 2.1 |
| 3 | 65.8 | 5.3 | 33.3 | 8.2 |
| 5 | 71.3 | 3.9 | 67.2 | 8.9 |
| 7 | 76.8 | 4.4 | 92.2 | 0.9 |
| 10 | 81.5 | 3.2 | 99.1 | 3.1 |

The results show that substantially more fluoxetine is released in the first 5 minutes by the tablet of the present invention than by the commercially available tablet. The differences at 1 and 3 minutes are statistically significant (Student's t-test, P<0.001; t values: 1 minute, 24.9; 3 minutes, 8.1).

EXAMPLE 4

Hardness Testing

Tablets of Composition B made by the method described in Example 1 were tested for hardness using a Computest Tablet Hardness Tester.

TABLE 4

Hardness Testing

| Tablet | Present Invention Hardness (Kp) | Commercially Available Hardness (Kp) |
|---|---|---|
| 1 | 4.2 | 33.3 |
| 2 | 3.3 | 27.9 |
| 3 | 3.7 | 29.3 |
| 4 | 4.2 | 33.3 |
| 5 | 4.4 | 29.7 |
| 6 | 4.7 | 33.3 |
| 7 | 4.4 | 29.7 |
| 8 | 3.7 | 33.1 |
| 9 | 4.3 | 29.3 |
| 10 | 4.3 | 30.1 |
| Average | 4.1 | 30.9 |
| SD | 0.4 | 2.1 |
| MINIMUM | 3.3 | 27.9 |
| MAXIMUM | 4.7 | 33.3 |

The difference in hardness between the tablets of the present invention and the commercially available tablets is highly significant (t-test: P<0.001, t=81.7), with the commercially available tablet on average more than seven times harder.

EXAMPLE 5

Disintegration Testing

Six tablets of Composition B made by the method described in Example 1 were tested for disintegration using the U.S.P. XXIII test for uncoated tablets. *United States Pharmacopoeia* XXIII: 1790–1791. All six tablets were completely disintegrated in 15 seconds. Six tablets of the commercially available fluoxetine formulation subjected to the same conditions were completely disintegrated in 4 minutes and 36 seconds.

The physical characteristics, such as hardness and disintegration, of the tablets of the present invention are significantly different from those of the commercially available tablet. These physical differences underlie the faster dissolving of the tablets of the present invention, and provide for bioavailability of the fluoxetine at a relatively more rapid rate for treating conditions such as premature ejaculation.

TABLE 5

Stability Testing

| Time (Weeks) | Composition A 7.5 mg Fluoxetine Base | | Composition B 15 mg Fluoxetine Base | |
|---|---|---|---|---|
| | Recovered Fluoxetine, % | Dissolution at 20 minutes, % (Average ± SD) | Recovered Fluoxetine, % | Dissolution at 20 minutes, % (Average ± SD) |
| 0 | 100.6[a] | 90.2 ± 6.0 | 98.4[a] | 97.8 ± 8.3 |
| 4 | 99.6[b] | 95.2 ± 7.6 | 99.6[b] | 104.6 ± 3.5 |
| 8 | 103.5[b] | 93.2 ± 7.3 | 104.1[b] | 99.5 ± 5.5 |
| 12 | 98.4[b] | 86.8 ± 8.5 | 99.6[b] | 89.7 ± 4.9 |
| 16 | 98.3[a] | 95.2 ± 7.5 | 100.0[a] | 94.5 ± 7.9 |
| 26 | 97.9[a] 100.1[b] | Not Available | 97.7[a] 98.9[b] | 89.3 ± 0.1 |

[a]Room Temperature (15–30 degrees Celsius)
[b]40 degrees Celsius, 75% Relative Humidity

EXAMPLE 6

Stability Testing

Tablets were made by the method of Example 1 and Example 2 were tested for stability by storage at room temperature (15–30 degrees Celsius) or elevated temperature and humidity (40 degrees Celsius, 75% Relative Humidity). The results are presented in Table 5, above.

The foregoing is intended to be illustrative of the present invention, but not limiting. Numerous variations and modifications of the present invention may be effected without departing from the true spirit and scope of the invention.

We claim:

1. A relatively low hardness, direct compression tablet that provides rapid dissolution of fluoxetine and which consists essentially of:

fluoxetine;

dicalcium phosphate dihydrate;

a disintegrant which is a microcrystalline cellulose;

a lubricant which is a magnesium stearate;

has a hardness not exceeding 6 kilopascals;

has a dicalcium phosphate dihydrate-to-disintegrant weight ratio in the range of about 3 to about 7: and has dissolution rate that provides the release of about 50 percent of the fluoxetine present in about one minute.

2. The tablet of claim 1 wherein the weight ratio of dicalcium phosphate dihydrate to microcrystalline cellulose is about 5.

3. The tablet of claim 1 containing about 7.5 milligrams to about 15 milligrams of fluoxetine, expressed as fluoxetine base.

4. The tablet of claim 1 containing about 7.5 to about 10 milligrams of fluoxetine, expressed as fluoxetine base.

5. The tablet of claim 1 wherein fluoxetine is present as fluoxetine hydrochloride.

6. The tablet of claim 1 having a hardness of about 2.5 to about 5.5 kilopascals.

7. The tablet of claim 1 having a hardness of about 3.5 to about 4.5 kilopascals.

8. The tablet of claim 1 having a hardness of about 4 kilopascals.

* * * * *